United States Patent [19]

Murray et al.

[11] Patent Number: 5,089,660
[45] Date of Patent: Feb. 18, 1992

[54] AROMATIC POLYCYANATE/MONOCYANATE COMONOMER COMPOSITIONS AND POLYTRIAZINES DERIVED THEREFROM

[75] Inventors: Daniel J. Murray; Mitchell G. Dibbs; Philip C. Yang, all of Midland, Mich.

[73] Assignee: The Dow Chemical Company, Midland, Mich.

[21] Appl. No.: 146,753

[22] Filed: Jan. 22, 1988

[51] Int. Cl.$^5$ .................. C07C 261/02; C07C 265/12
[52] U.S. Cl. .................... 560/301; 558/418; 558/419; 558/470; 558/422; 560/106; 560/109; 560/110; 560/142; 560/250
[58] Field of Search ........... 560/301, 100, 106, 109, 560/110, 142; 558/422; 544/193, 219

[56] References Cited

U.S. PATENT DOCUMENTS

| | | | |
|---|---|---|---|
| 3,553,244 | 1/1971 | Grigat et al. | 560/301 |
| 4,528,366 | 7/1985 | Woo et al. | 544/193 X |
| 4,740,584 | 4/1988 | Shimp | 528/422 |
| 4,746,727 | 5/1988 | Bogan et al. | 528/422 X |
| 4,748,270 | 5/1988 | Murray et al. | 560/301 |
| 4,751,323 | 6/1988 | Woo et al. | 560/301 |
| 4,782,178 | 11/1988 | Godschalx et al. | 560/301 |
| 4,806,625 | 2/1989 | Bogan et al. | 528/422 |

FOREIGN PATENT DOCUMENTS 877840  9/1961  United Kingdom ................ 560/301

OTHER PUBLICATIONS

Korshak, et al., Polymer Science USSR, A17, No. 1, pp. 24–30, (1975).
Brand et al., NASA Contractor Report 3185 (1975), pp. 2–21.
Grigat et al., Angew. Chem. 79, (1967), pp. 209–221.

Primary Examiner—Joseph Paul Brust

[57] ABSTRACT

A comonomer composition of an aromatic polycyanate and an aromatic monocyanate substituted at each position ortho to the cyanate group, and a polytriazine copolymer derived therefrom.

32 Claims, No Drawings

AROMATIC POLYCYANATE/MONOCYANATE COMONOMER COMPOSITIONS AND POLYTRIAZINES DERIVED THEREFROM

BACKGROUND OF THE INVENTION

This invention relates to a comonomer composition of an aromatic polycyanate and an aromatic monocyanate, and polytriazines derived therefrom. More specifically, it relates to these compositions when the aromatic monocyanate is substituted at each position ortho to the cyanate group.

Polycyanate monomers are well-known thermosets that polymerize to form polytriazines. Polytriazines possess good heat resistance, hardness, electrical properties, dimensional stability, corrosion resistance, and chemical resistance. They are useful as adhesives and as coatings for substrates. They are also useful for the preparation of advanced composites and for the preparation of electrical laminates.

Attempts have been made to enhance the physical properties of polytriazines by incorporating various phenyl monocyanates into aromatic polycyanates before cure. For example, phenyl cyanate and phenyl cyanate substituted at the para position have been used as comonomers to modify polytriazines prepared from aromatic polycyanates. Korshak et al., *Polymer Science USSR*, A17: No. 1, p. 23-27, 1975, disclose modified physical and mechanical properties of a polytriazine prepared from the dicyanate of bisphenol A and varying amounts of phenyl cyanate. This polytriazine is believed to be represented by the formula:

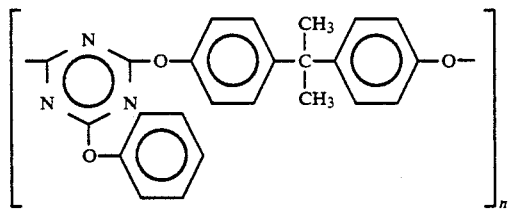

Brand et al., *NASA Contractor Report* 3185, 1979, disclose reduced water sorption of polytriazines prepared from dioyanates and varying amounts of either 4-nonylphenyl cyanate or 4-phenylphenyl cyanate.

Unfortunately, even though the addition of the phenyl cyanates employed in the art reduces water sorption of the prepared polytriazine, other physical and mechanical properties of the polytriazine are adversely affected. Most significantly, Korshak et al., supra, disclose a significant reduction in toughness, as measured by impact strength, relative to a polytriazine prepared without the addition of a phenyl cyanate.

In view of the deficiencies of the prior art, a polytriazine with enhanced physical properties derived from a comonomer composition of an aromatic polycyanate and an aromatic monocyanate is needed. More particularly, a polytriazine derived from such a comonomer composition with increased toughness and overall outstanding physical properties is needed.

SUMMARY OF THE INVENTION

In one aspect, the invention is a comonomer composition comprising an aromatic polycyanate and an aromatic monocyanate substituted at each position ortho to the cyanate group.

In another aspect, the invention is a polytriazine comprising a copolymer of an aromatic polycyanate and an aromatic monocyanate substituted at each position ortho to the cyanate group.

Surprisingly, the polytriazines prepared from the comonomer compositions of this invention exhibit improved toughness relative to polytriazines prepared from a polycyanate alone. Other physical properties, such as stiffness and heat resistance, are not adversely affected, and in fact, may actually improve with the addition of the substituted aromatic monocyanate.

The polytriazines of this invention are useful for preparing advanced composites and fiber-reinforced laminates, and for any other application where polytriazines are used.

DETAILED DESCRIPTION OF THE INVENTION

Aromatic polycyanates are disclosed in U.S. Pat. Nos. 3,553,244; 3,738,962; 4,396745; 4,528,366; 4,559,399; and 4,581,425. Preferred aromatic polycyanates are prepared from the polyhydric phenols of bisphenol A and bisphenol S, halogenated and/or alkylated analogs of bisphenol A and bisphenol S, novolaks, and polyphenols bridged by one or more polycyclic aliphatic groups as described in U.S. Pat. No. 4,528,366. More preferred aromatic polycyanates are prepared from the polyhydric phenols of bisphenol A and halogenated analogs of bisphenol A, and polyphenols bridged by one or more polycyclic aliphatic groups. The most preferred aromatic polycyanates are prepared from polyphenols bridged by one or more polycyclic aliphatic groups. An especially preferred aromatic polycyanate has the following formula:

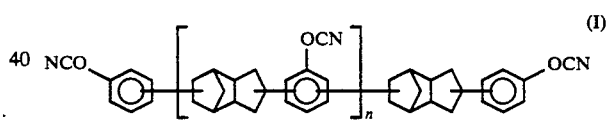
(I)

wherein the average value of n is about 0.2.

A process for preparing the most preferred aromatic polycyanate and other preferred aromatic polycyanates is disclosed in copending U.S. application Ser. No. 552,515, filed Nov. 16, 1983, now issued as U.S. Pat. No. 4,748,270 (May 31, 1988).

The aromatic monocyanates within the scope of this invention are substituted at each position ortho to the cyanate group. Each ortho position refers to each position on the aromatic ring adjacent to the position having the carbon-cyanate bond. Substitution refers to the replacement of hydrogen from a carbon-hydrogen bond on the aromatic ring with either halo or any other radical. The radical can be monovalent, or divalent wherein the radical forms part of a fused ring.

Although the mechanism by which the aromatic monocyanates increase toughness of polytriazines is unclear, it is believed that the ortho substituents of the monocyanate sterically hinder reaction of the monocyanate with itself and thus allow increased reaction with the aromatic polycyanate. The reaction between the monocyanate and the polycyanate reduces the crosslink density of the prepared polytriazine and increases toughness. Therefore, any substitution that sterically hinders reaction of the cyanate group on the aromatic monocyanate and is stable during the polymerization reaction is adequate. For purposes of determining steric hindrance, if the prepared polytriazine exhibits increased toughness relative to the toughness exhibited by a polytriazine prepared by the homopolymerization of an aromatic polycyanate, then the substitution is presumed to sterically hinder reaction.

Although any aromatic monocyanate having a hydrocarbyl nucleus and substituted at each position ortho to the cyanate group can be used as a comonomer, the preferred substituted monocyanates are phenyl, naphthyl, anthracyl, and phenanthryl monocyanates independently substituted at each position ortho to the cyanate group with halo, straight or branched $C_{1-4}$ alkyl, phenyl or substituted phenyl, mercapto, cyano, formyl, Y—O—, Y—S—, Y—CO—, Y—COO—, or substituted methyl wherein Y is $C_{1-4}$ alkyl, or phenyl or substituted phenyl. "Substituted phenyl" refers to phenyl substituted with halo or methyl, or any other substituent that does not adversely affect the properties of the prepared polytriazine. "Substituted methyl" refers to X—CH$_2$—, Y—OCH$_2$—, Y—SCH$_2$—, Y—COCH$_2$—, or Y—COOCH$_2$—; wherein X is halo, phenyl or substituted phenyl, mercapto, formyl, or cyano; and Y is defined as previously defined. Preferably, the aromatic monocyanate is independently substituted at each position ortho to the cyanate group with halo, straight or branched $C_{1-4}$ alkyl, or substituted methyl. Preferred substituted methyl are X—CH$_2$—, Y—OCH$_2$—, or Y—COOCH$_2$—; wherein X is halo, phenyl or substituted phenyl, or cyano; and Y is defined as previously defined.

Preferably, the substituted monocyanates are either phenyl or naphthyl cyanates. Preferred naphthyl cyanates are derived from 1-naphthyl cyanate and 2-naphthyl cyanate. For purposes of describing this invention, substitution on the naphthalene ring will be designated as follows:

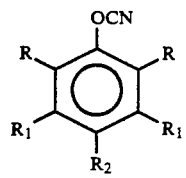

A preferred class of naphthyl cyanates is 1-naphthyl cyanate substituted at the 2 position and inherently at the 9 position, and alternatively, further substituted at the 8 position. Another preferred naphthyl cyanate is 2-naphthyl cyanate substituted at the 1 and 3 positions. The preferred substituents are methyl, bromo, and chloro.

The most preferred aromatic monocyanates are phenyl cyanates. Advantageously, the phenyl cyanates are represented by the formula:

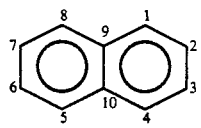

wherein
each R is independently halo, straight or branched $C_{1-4}$ alkyl, phenyl or substituted phenyl, mercapto, cyano, formyl, Y—O—, Y—S, Y—CO—, Y—COO—, X—CH$_2$—, Y—OCH$_2$—, Y—SCH$_2$—, Y—COCH$_2$—, or Y—COOCH$_2$—;

each $R_1$ is independently hydrogen, halo, $C_{1-4}$ alkyl, $C_{1-4}$ alkoxy or thioalkoxy (i.e., alkylthio), or cyano;

$R_2$ is hydrogen, halo, straight or branched $C_{1-4}$ alkyl, phenyl or substituted phenyl, mercapto, cyano, formyl, Y—O—, Y—S—, Y—CO—, Y—COO—, X—CH$_2$—, Y—OCH$_2$—, Y—SCH$_2$—, Y—COCH$_2$—, or Y—COOCH$_2$—;

X is halo, phenyl or substituted phenyl, mercapto, formyl, or cyano; and

Y is $C_{1-4}$ alkyl, or phenyl or substituted phenyl.

Halogenated phenyl cyanates represented by the formula above not only improve toughness of the prepared polytriazine but also increase fire resistance as well. It is well known in the art to improve fire resistance of polytriazines by incorporating therein halogen-containing substances. See, for example, U.S. Pat. No. 4,097,455.

Preferably, the phenyl cyanates are represented by the formula:

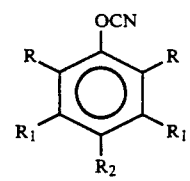

wherein
each R is independently halo, straight or branched $C_{1-4}$ alkyl, X—CH$_2$—, Y—OCH$_2$—, Y—SCH$_2$—, Y—COCH$_2$—, or Y—COOCH$_2$—;

each $R_1$ is independently hydrogen, halo, $C_{1-4}$ alkyl, $C_{1-4}$ alkoxy or thioalkoxy, or cyano;

$R_2$ is hydrogen, halo, straight or branched $C_{1-4}$ alkyl, phenyl or substituted phenyl, mercapto, cyano, formyl, Y—O—, Y—S—, Y—CO—, Y—COO—, X—CH$_2$—, Y—OCH$_2$—, Y—SCH$_2$—, Y—COCH$_2$—, or Y—COOCH$_2$—;

X is halo, phenyl or substituted phenyl, mercapto, formyl, or cyano; and

Y is $C_{1-4}$ alkyl, or phenyl or substituted phenyl.

A more preferred class of phenyl cyanates is represented by the formula:

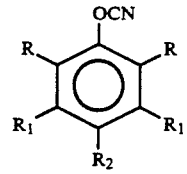

wherein
each R is independently halo, straight or branched $C_{1-4}$ alkyl, X—CH$_2$—, Y—OCH$_2$—, or Y—COOCH$_2$—;

each $R_1$ is independently hydrogen, halo, $C_{1-4}$ alkyl, $C_{1-4}$ alkoxy or thioalkoxy, or cyano;

$R_2$ is hydrogen, halo, straight or branched $C_{1-4}$ alkyl, phenyl or substituted phenyl, cyano, Y—O—, X—CH$_2$—, Y—OCH$_2$—, Y—COOCH$_2$;

X is halo, phenyl or substituted phenyl, or cyano;

Y is $C_{1-4}$ alkyl, or phenyl or substituted phenyl.

Preferred straight or branched $C_{1-4}$ alkyl are methyl, secondary or tertiary butyl, and isopropyl, and the phenyl cyanates are represented by the formula:

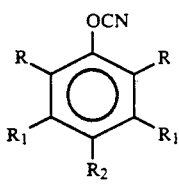

wherein each R is independently halo, methyl, methoxymethyl, acetoxymethyl, secondary or tertiary butyl, or isopropyl;

each $R_1$ is independently hydrogen, halo, methyl, methoxy, or cyano; and $R_2$ is hydrogen, halo, methyl, methoxymethyl, acetoxymethyl, secondary or tertiary butyl, isopropyl, methoxy, cyano, phenyl, phenyloxy, or benzyl.

An even more preferred class is represented by the formula:

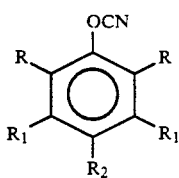

wherein each R is independently halo, methyl, methoxymethyl, acetoxymethyl, secondary or tertiary butyl, or isopropyl;

each $R_1$ is independently hydrogen, halo, or methyl; and $R_2$ is hydrogen, halo, methyl, methoxymethyl, aoetoxymethyl, secondary or tertiary butyl, or isopropyl.

Preferably, the class of substituents at the para position is limited to a preferred class of substituents at the meta positions, and the phenyl cyanate is represented by the formula:

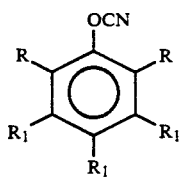

wherein each R is independently methyl, methoxymethyl, acetoxymethyl, secondary butyl, or isopropyl; and each $R_1$ is independently hydrogen, chloro, bromo, or methyl.

The preferred substituents at the meta and para positions are hydrogen, bromo, and methyl; and the phenyl cyanate is represented by the formula:

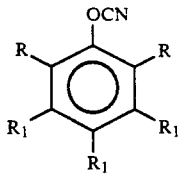

wherein each R is independently methyl, methoxymethyl, acetoxymethyl, secondary butyl, or isopropyl; and each $R_1$ is independently hydrogen, bromo, or methyl.

A more preferred class of phenyl cyanates is represented by the formula:

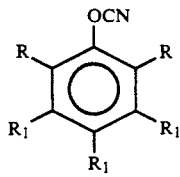

wherein each R is independently methyl, methoxymethyl, secondary butyl, or isopropyl; and each $R_1$ is independently hydrogen, bromo, or methyl.

The most preferred class of phenyl cyanates is depicted when both ortho positions are substituted with methyl, isopropyl, or secondary butyl. The class is represented by the formula:

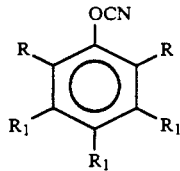

wherein

R is methyl, isopropyl, or secondary butyl; and each $R_1$ is independently hydrogen, bromo, or methyl.

Preferably, each meta position and the para position is independently substituted with bromo or methyl, and the class of phenyl cyanates is represented by the formula:

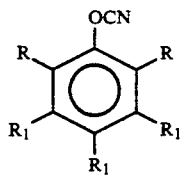

wherein

R is methyl, isopropyl, or secondary butyl; and each $R_1$ is independently bromo or methyl.

The most preferred phenyl cyanates are depicted when both ortho substituents are methyl and both meta substituents are bromo. These halogenated cyanates are represented by the formula:

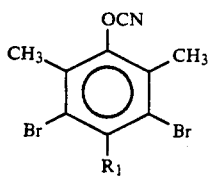

wherein $R_1$ is bromo or methyl.

The most preferred phenyl cyanates are 2,4,6-trimethyl-3,5-dibromophenyl cyanate, which is represented by the formula:

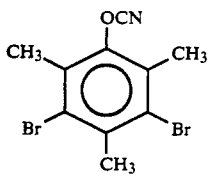

and 2,6-dimethyl-3,4,5-tribromophenyl cyanate, which is represented by the formula:

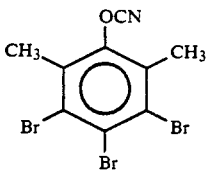

Processes for preparing the most preferred phenyl cyanates and other aromatic monocyanates are disclosed in copending U.S. application Ser. No. 120,310, filed Nov. 13, 1987, now issued as U.S. Pat. No. 4,782,178 (Nov. 1, 1988) which is incorporated by reference herein.

The most preferred comonomer compositions are compositions of either 2,4,6-trimethyl-3,5-dibromophenyl cyanate or 2,6-dimethyl-3,4,5-tribromophenyl cyanate and the aromatic polycyanate represented by formula I.

The comonomer composition can be a mixture of two or more aromatic monocyanates within the scope of this invention and an aromatic polycyanate. The comonomer composition can also be a mixture of two or more aromatic polycyanates and a suitable aromatic monocyanate. Likewise, the comonomer composition can be a mixture of two or more suitable aromatic monocyanates and two or more aromatic polycyanates.

The comonomers can be blended in any manner effective to prepare a homogeneous mixture. If the polycyanate is a solid or viscous liquid at room temperature, a homogeneous mixture can be prepared by first melting the polycyanate at an elevated temperature and then mixing the monocyanate with the melted polycyanate. Alternatively, the homogeneous mixture can be prepared by dissolving the polycyanate in a suitable solvent, mixing the solution with the monocyanate, and then removing the solvent.

The amount of monocyanate incorporated into the comonomer composition is an amount effective to provide the desired degree of toughness to the prepared polytriazine. Preferably, the composition contains from about 1 to about 50 percent monocyanate, more preferably from about 5 to about 30 percent monocyanate. Percent is defined as the percent of cyanate groups derived from the aromatic monocyanate. For example, a comonomer composition containing 2 moles of an aromatic dicyanate and 1 mole of an aromatic monocyanate contains 20 percent monocyanate.

Reactive and nonreactive additives can be added to the comonomer composition to improve the physical, chemical, or electrical properties of the prepared polytriazine. Reactive additives include aromatic monocyanates not within the scope of this invention, as well as other cyanate-reactive monomers. Nonreactive additives include grafted rubber particles to increase toughness, as described in copending U.S. application Ser. No. 79,378, filed July 30, 1987, now U.S. Pat. No. 4,894,414, halogen-containing substances to improve fire resistance, and antioxidants to improve thermal stability.

The comonomer composition can be cured to form the polytriazine. The composition is cured in a manner similar to the curing of an aromatic polycyanate that does not contain an aromatic monocyanate. The composition can be cured thermally without the use of a catalyst. Preferably, a catalyst is used. U.S. Pat. Nos. 3,694,410; 4,094,852; and 4,528,366 disclose suitable catalysts. Preferred catalysts are cobalt catalysts such as cobalt acetylacetonate, cobalt octoate, and cobalt naphthenate. The amount of catalyst can range from about 10 ppm to about 1000 ppm based on the weight of comonomer composition.

The following example is illustrative and does not limit the scope of this invention.

EXAMPLE

For each of a series of runs, a homogeneous blend of the preferred aromatic polycyanate of formula 1 and an amount of one of the aromatic monocyanates designated as Samples 1-7 in Table 1 is prepared. 100 ppm cobalt as cobalt acetylacetonate is added to the blend. The blend is cured for 1 hour at 175° C. 2 hours at 225° C., and 1 hour at 250° C. using standard casting techniques. The castings are then analyzed to determine the physical properties of the prepared polytriazine. The results are illustrated in Table 2.

TABLE I

| Sample No | Samples of Aromatic Monocyanates Used as Comonomers |
|---|---|
| | Monocyanate Comonomer |
| 1* | phenyl cyanate |
| 2* | nonylphenyl cyanate |
| 3 | 2,6-dimethylphenyl cyanate |
| 4 | 2,6-dimethylphenyl cyanate |
| 5 | 2,6-dimethylphenyl cyanate |
| 6 | 2,4,6-trimethyl-3,5-dibromophenyl cyanate |
| 7 | 2,4,6-trimethyl-3,5-dibromophenyl cyanate |

*Not an embodiment of this invention.

TABLE II

Physical Properties of Polytriazines Prepared From a Preferred Aromatic Polycyanate and Varying Aromatic Monocyanates

| Sample No | Amount of Aromatic Monocyanate in Comonomer Composition Cyanate Equivalent Percent | Dry Shear Modulus[1] of Polytriazine (1000 psi at 180° F.) | Wet Shear Modulus[2] of Polytriazine (1000 psi at 180° F.) | $G_{IC}$[3] (J/m²) of Polytriazine | Dry $T_g$[4] (°C.) of Polytriazine | Wet $T_g$[5] (°C.) of Polytriazine |
|---|---|---|---|---|---|---|
| control* | 0 | 159 | 186 | 60 | 255 | 215 |
| 1* | 9.6 | 174 | 153 | 98 | 237 | Not measured |
| 2* | 9.6 | 152 | 158 | 100 | 218 | 204 |
| 3 | 6.4 | 160 | 180 | 99 | 247 | 207 |
| 4 | 12.6 | 174 | 188 | 127 | 224 | 200 |
| 5 | 18.0 | 172 | 189 | 168 | 202 | 183 |
| 6 | 9.6 | 166 | 184 | 115 | 239 | 218 |
| 7 | 13.0 | 179 | 192 | 133 | 230 | 217 |

*Not an embodiment of this invention
[1] Determined by dynamic mechanical spectroscopy (DMS)
[2] Determined by DMS after boiling the polytriazine in water for 500 hours
[3] GIC is the fracture energy as measured by compact tension according to ASTM procedure E-399
[4] Tg is the glass transition temperature as determined by DMS
[5] Determined by DMS after boiling the polytriazine in water for 500 hours.

The data in Table 2 indicates that the polytriazines of this invention exhibit not only increased toughness, as indicated by the increase in fracture energy, but also improved stiffness, as indicated by the increase in shear modulus. These improved properties are obtained without significantly sacrificing the heat resistance of the polytriazine, as measured by the glass transition temperature. Conversely, the shear modulus of the polytriazine, especially the wet shear modulus, decreases significantly relative to the unmodified polytriazine (control) when an aromatic monocyanate not within the scope of this invention is used as the comonomer.

Upon repeating the procedure of this example with other aromatic polycyanates and aromatic monocyanates within the scope of this invention, similar excellent results are obtained.

What is claimed is:

1. A comonomer composition which is curable to form a cured polytriazine product, said composition comprising at least one aromatic polycyanate and at least one aromatic monocyanate having a hydrocarbyl nucleus and substituted at each position ortho to the cyanate group, said aromatic monocyanate(s) being present in an amount effective to cause the cured polytriazine product of the comonomer composition to have impact strength higher than the impact strength of a cured polytriazine product of the aromatic polycyanate alone.

2. The comonomer composition of claim 1 wherein the aromatic polycyanate is a polycyanate of bisphenol A or bisphenol S, a halogenated and/or alkylated analog of bisphenol A or bisphenol S, a novolak, or a polyphenol bridged by at least one polycyclic aliphatic group.

3. The comonomer composition of claim 2 wherein the aromatic polycyanate is a polycyanate of bisphenol A, a halogenated analog of bisphenol A, or a polyphenol bridged by at least one polycyclic aliphatic group.

4. The comonomer composition of claim 3 wherein the aromatic polycyanate is a polycyanate of a polyphenol bridged by at least one polycyclic aliphatic group.

5. The comonomer composition of claim 4 wherein the aromatic polycyanate has the formula:

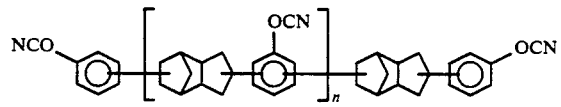

wherein the average value of n is about 0.2

6. The comonomer composition of claim 1 wherein the aromatic monocyanate is a phenyl cyanate, a naphthyl cyanate, an anthracyl cyanate, or a phenanthryl cyanate.

7. The comonomer composition of claim 6 wherein the aromatic monocyanate is a phenyl cyanate or a naphthyl cyanate.

8. The comonomer composition of claim 7 wherein the naphthyl cyanate is a 1-naphthyl cyanate substituted at the 2 position.

9. The comonomer composition of claim 8 wherein the 1-naphthyl cyanate is substituted at the 2 position with methyl, bromo, or chloro.

10. The comonomer composition of claim 8 wherein the 1-naphthyl cyanate is further substituted at the 8 position.

11. The comonomer composition of claim 10 wherein the 1-naphthyl cyanate is substituted at each of the 2 and 8 positions independently with methyl, bromo, or chloro.

12. The comonomer composition of claim 7 wherein the naphthyl cyanate is a 2naphthyl cyanate substituted at each of the 1 and 3 positions.

13. The comonomer composition of claim 12 wherein the 2naphthyl cyanate is substituted at each of the 1 and 3 positions independently with methyl, bromo, or chloro.

14. The comonomer composition of claim 7 wherein the aromatic monocyanate is a phenyl cyanate.

15. The comonomer composition of claim 14 wherein the phenyl cyanate is represented by the formula:

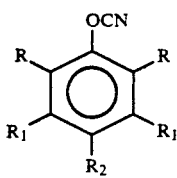

wherein
  each R is independently halo, straight or branched C$_{1-4}$ alkyl, phenyl or substituted phenyl, mercapto, cyano, formyl, Y—O—, Y—S, Y—CO—, Y—COO—, —X—CH$_2$—, Y—OCH$_2$—, Y—SCH$_2$—, Y—COCH$_2$—, or Y—COOCH$_2$—;
  each R$_1$ is independently hydrogen, halo, C$_{1-4}$ alkyl, C$_{1-4}$ alkoxy or alkylthio, or cyano;
  R$_2$ is hydrogen, halo, straight or branched C$_{1-4}$ alkyl, phenyl or substituted phenyl, mercapto, cyano, formyl, Y—O—, Y—S—, Y—CO—, Y—COO—, X—CH$_2$—, Y—OCH$_2$—, Y—SCH$_2$—, Y—COCH$_2$—, or Y—COOCH$_2$—;
  X is halo, phenyl or substituted phenyl, mercapto, formyl, or cyano; and
  Y is C$_{1-4}$ alkyl, or phenyl or substituted phenyl.

16. The comonomer composition of claim 15 wherein the phenyl cyanate is represented by the formula:

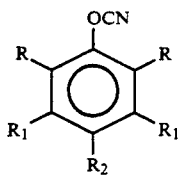

wherein
  each R is independently halo, straight or branched C$_{1-4}$ alkyl, —X—CH$_2$—, Y—OCH$_2$—, Y—SCH$_2$—, Y—COCH$_2$—, or Y—COOCH$_2$—;
  each R$_1$ is independently hydrogen, halo, C$_{1-4}$ alkyl, C$_{1-4}$ alkoxy or alkylthio or cyano;
  R$_2$ is hydrogen, halo, straight or branched C$_{1-4}$ alkyl, phenyl or substituted phenyl, mercapto, cyano, formyl, Y—O—, Y—S—, Y—CO—, Y—COO—, X—CH$_2$—, Y—OCH$_2$—, Y—SCH$_2$—, Y—COCH$_2$—, or Y—COOCH$_2$—;
  X is halo, phenyl or substituted phenyl, mercapto, formyl, or cyano; and
  Y is C$_{1-4}$ alkyl, or phenyl or substituted phenyl.

17. The comonomer composition of claim 15 wherein the phenyl cyanate is represented by the formula:

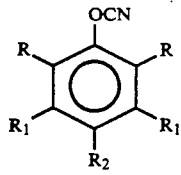

wherein
  each R is independently halo, straight or branched C$_{1-4}$ alkyl, X—CH$_2$—, Y—OCH$_2$—, or Y—COOCH$_2$—;
  each R$_1$ is independently hydrogen, halo, C$_{1-4}$ alkyl, C$_{1-4}$ alkoxy or alkylthio, or cyano;
  R$_2$ is hydrogen, halo, straight or branched C$_{1-4}$ alkyl, phenyl or substituted phenyl, cyano, Y—O—, X—CH$_2$—, Y—OCH$_2$—, or Y—COOCH$_2$—;
  X is halo, phenyl or substituted phenyl, or cyano;
  Y is C$_{1-4}$ alkyl, or phenyl or substituted phenyl.

18. The comonomer composition of claim 15 wherein the phenyl cyanate is represented by the formula:

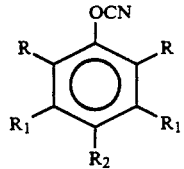

wherein
  each R is independently halo, methyl, methoxymethyl, acetoxymethyl, secondary or tertiary butyl or isopropyl;
  each R$_1$ is independently hydrogen, halo, methyl, methoxy, or cyano; and
  R$_2$ is hydrogen, halo, methyl, methoxymethyl, acetoxymethyl, secondary or tertiary butyl, isopropyl, methoxy, cyano, phenyl, phenyloxy, or benzyl.

19. The comonomer composition of claim 18 wherein the phenyl cyanate is represented by the formula:

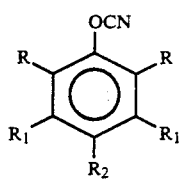

wherein
  each R is independently halo, methyl, methoxymethyl, acetoxymethyl, secondary or tertiary butyl, or isopropyl;
  each R$_1$ is independently hydrogen, halo, or methyl; and
  R$_2$ is hydrogen, halo, methyl, methoxymethyl, acetoxymethyl, secondary or tertiary butyl, or isopropyl.

20. The comonomer composition of claim 19 wherein the phenyl cyanate is represented by the formula:

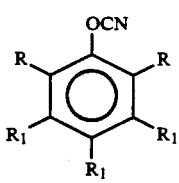

wherein
  each R is independently methyl, methoxymethyl, acetoxymethyl, secondary butyl, or isopropyl; and
  each R$_1$ is independently hydrogen, chloro, bromo, or methyl.

21. The comonomer composition of claim 20 wherein the phenyl cyanate is represented by the formula:

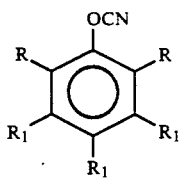

wherein
each R is independently methyl, methoxymethyl, acetoxymethyl, secondary butyl, or isopropyl; and
each $R_1$ is independently hydrogen, bromo, or methyl.

22. The comonomer composition of claim 21 wherein the phenyl cyanate is represented by the formula:

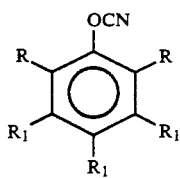

wherein
each R is independently methyl, methoxymethyl, secondary butyl, or isopropyl; and
each $R_1$ is independently hydrogen, bromo, or methyl.

23. The comonomer composition of claim 22 wherein the phenyl cyanate is represented by the formula:

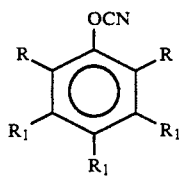

wherein
R is methyl, isopropyl, or secondary butyl; and
each $R_1$ is independently hydrogen, bromo, or methyl.

24. The comonomer composition of claim 23 wherein the phenyl cyanate is represented by the formula:

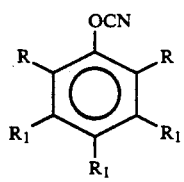

wherein
R is methyl, isopropyl, or secondary butyl; and
each $R_1$ is independently bromo or methyl.

25. The comonomer composition of claim 24 wherein the phenyl cyanate is represented by the formula:

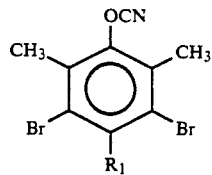

wherein $R_1$ is bromo or methyl.

26. The comonomer composition of claim 25 wherein the phenyl cyanate is represented by the formula:

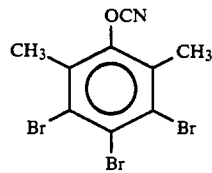

27. The comonomer composition of claim 26 wherein the phenyl cyanate is represented by the formula:

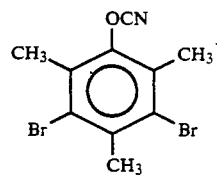

28. The comonomer composition of claim 26 wherein the aromatic polycyanate is represented by the formula:

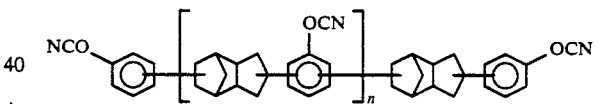

wherein the average value of n is about 0.2.

29. The comonomer composition of claim 27 wherein the aromatic polycyanate is represented by the formula:

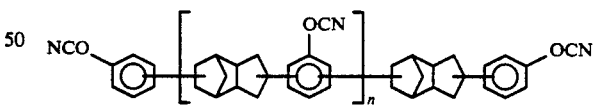

wherein the average value of n is about 0.2.

30. The comonomer composition of claim 1 wherein between about 1 percent and about 30 percent of the cyanate groups in the comonomer composition are derived from the aromatic monocyanate(s).

31. The comonomer composition of claim 1 wherein between about 5 percent and about 30 percent of the cyanate groups in the comonomer composition are derived from the aromatic monocyanate(s).

32. The comonomer composition of claim 5 wherein the aromatic monocyanate contributes between about 5 percent and about 30 percent of the cyanate groups in the comonomer composition and is represented by the formula:

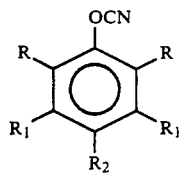
wherein
each R is independently halo, methyl, methoxymethyl, acetoxymethyl, secondary or tertiary butyl, or isopropyl;
each $R_1$ is independently hydrogen, halo, methyl, methoxy, or cyano; and
$R_2$ is hydrogen, halo, methyl, methoxymethyl, acetoxymethyl, secondary or tertiary butyl, isopropyl, methoxy, cyano, phenyl, phenyloxy, or benzyl.
* * * * *